United States Patent
Johnson

(10) Patent No.: US 11,623,905 B2
(45) Date of Patent: Apr. 11, 2023

(54) ISOLATION AND CRYSTALLIZATION OF CANNABINOIDS WITHOUT DISTILLATION OR EVAPORATION OF SOLVENTS

(71) Applicant: EnCann Solutions Inc., Kelowna (CA)

(72) Inventor: Lawerance Lincoln Johnson, Kelowna (CA)

(73) Assignee: ENCANN SOLUTIONS INC., Kelowna (CA)

( * ) Notice: Subject to any disclaimer, the term of this patent is extended or adjusted under 35 U.S.C. 154(b) by 0 days.

(21) Appl. No.: 17/740,766

(22) Filed: May 10, 2022

(65) Prior Publication Data

US 2022/0371977 A1 Nov. 24, 2022

Related U.S. Application Data

(60) Provisional application No. 63/186,695, filed on May 10, 2021.

(51) Int. Cl.
*C07C 37/84* (2006.01)

(52) U.S. Cl.
CPC .................... *C07C 37/84* (2013.01)

(58) Field of Classification Search
CPC ...................................... C07C 37/84
See application file for complete search history.

(56) References Cited

U.S. PATENT DOCUMENTS

| 11,345,650 B1 * | 5/2022 | Drennan ................ C07C 37/84 |
| 11,465,957 B1 * | 10/2022 | Drennan .............. C07D 311/00 |
| 2021/0023155 A1 * | 1/2021 | Opperman .......... B01D 11/0288 |
| 2021/0402325 A1 * | 12/2021 | Naito .................... B01D 9/0013 |

* cited by examiner

*Primary Examiner* — Sikarl A Witherspoon
(74) *Attorney, Agent, or Firm* — Stefan J. Kirchanski; Matthew J. Spark; Zuber Lawler LLP

(57) ABSTRACT

Cannabis plant material is extracted with a solvent matrix consisting of one or more organic solvents and optionally water. The cannabis plant material is agitated in the solvent matrix and then removed by filtration or centrifugation. Following extraction, the plant material is separated from the solvent matrix by centrifugation. The resulting extract is clarified by membrane filtration which also removes most of the water and water-soluble impurities. The resulting extract is dewaxed using membrane filtration and/or liquid-liquid extraction. Excess solvent and terpenoids are removed by means of molecular weight cutoff membrane filtration and the resulting cannabinoid solution is decarboxylated catalytically. Seed crystals are added to crystallize the cannabinoids.

6 Claims, 4 Drawing Sheets

| Process Flow Diagram for Isolate Production ||||||
|---|---|---|---|---|
| Material Added || Step | Material Removed ||
| 200 | kg Milled *Cannabis Sativa* | EXTRACTION ↓ | | |
| 16 | kg total CBD in biomass ||||
| 600 | L alkane ||||
| 1000 | L Water → ||||
| | | SEPARATION → ↓ | 175 | kg biomass waste |
| | | | 12 | L alkane in waste |
| | | | 50 | L water in waste |
| | | | 0.32 | kg CBD lost in alkane waste |
| | | CLARIFYING → ↓ | 9 | kg biomass waste |
| | | | 6 | L alkane in waste |
| | | | 950 | L water removed |
| | | | 0.2 | kg CBD lost in alkane waste |
| | | DEWAXING → ↓ | 0.4 | kg CBD lost in waxes |
| | | DESOLVATION → ↓ | 0.2 | kg CBD lost in desolvation |
| | | | 548 | L alkane reclaim |
| 14.9 | g MgO → | DECARBOXYLATION ↓ | | |
| 1.71 | kg salt | BRINE WASH → ↓ | 1.71 | kg salt |
| 34.3 | L water → | | 34.3 | L water |
| | | | 14.9 | g MgO |
| 0.16 | kg Seed crystal | CRYSTALLIZATION ↓ | | |
| 0.4 | L alkane → | | | |
| 8 | L alkane wash | FILTRATION/WASH → ↓ | 42 | L Mother Liquor to desolve |
| | → | | 3 | kg CBD in Mother |
| 24 | L water wash | | 24 | L water |

12 kg CBD Crystals

Fig. 2

|  |  | Running total |  |  | |
|---|---|---|---|---|---|
| Biomass (kg) | CBD (kg) | Alkane (L) | Water (L) | Biomass (L) | Op. Vol (L) |
| 184 | 0.000 | 0.000 | 0.000 | 1472 | 1472 |
| 184 | 16.000 | 0.000 | 0.000 | 1472 | 1488 |
| 184 | 16.000 | 600.000 | 0.000 | 1472 | 2088 |
| 184 | 16.000 | 600.000 | 1000.000 | 1472 | 3088 |
| | | | | | |
| 9.2 | 16.000 | 600.000 | 1000.000 | 74 | 1690 |
| 9.2 | 16.000 | 588.000 | 1000.000 | 74 | 1678 |
| 9.2 | 16.000 | 588.000 | 950.000 | 74 | 1628 |
| 9.2 | 15.680 | 588.000 | 950.000 | 74 | 1627 |
| | | | | | |
| 0 | 15.680 | 588.000 | 950.000 | 0 | 1554 |
| 0 | 15.680 | 582.120 | 950.000 | 0 | 1548 |
| 0 | 15.680 | 582.120 | 0.000 | 0 | 598 |
| 0 | 15.523 | 582.120 | 0.000 | 0 | 598 |
| | | | | | |
| 0 | 15.135 | 582.120 | 0.000 | 0 | 597 |
| | | | | | |
| 0 | 15.135 | 582.120 | 0.000 | 0 | 597 |
| 0 | 14.908 | 582.120 | 0.000 | 0 | 597 |
| 0 | 14.908 | 34.289 | 0.000 | 0 | 49 |
| | | | | | |
| 0 | 14.908 | 34.289 | 0.000 | 0 | 49 |
| | | | | | |
| 0 | 14.908 | 34.289 | 0.000 | 0 | 49 |
| 0 | 14.908 | 34.289 | 0.000 | 0 | 49 |
| 0 | 14.908 | 34.289 | 0.000 | 0 | 49 |
| | | | | | |
| 0 | 15.068 | 34.289 | 0.000 | 0 | 49 |
| 0 | 15.068 | 34.657 | 0.000 | 0 | 50 |
| | | | | | |
| 0 | 15.068 | 0.000 | 0.000 | 0 | 15 |
| 0 | 12.054 | 0.000 | 0.000 | 0 | 12 |
| 0 | 12.054 | 0.000 | 0.000 | 0 | 12 |

Fig. 3

| | | | | | |
|---|---|---|---|---|---|
| 200 | kg biomass | | | | |
| 8.00% | CBD | | | | |
| 0.0267 | kg CBD / L alkane | 3 | 1 | L alkane : kg biomass | |
| 5 | GPM water consumption | 5 | | L water : kg biomass | |
| 51 | L/min process flow | 8 | 1 | Total solvent : kg biomass | |
| 14 | GPM process flow | | | | |
| 95.00% | % of biomass removed | | | | |
| 2.00% | alkane lost with biomass | | | | |
| 5.00% | Water lost with biomass | | | | |
| 7 | GPM clairifying | | | | |

| | |
|---|---|
| 1.00% | alkane lost with biomass |
| 5.00% | Water lost with biomass |

| | |
|---|---|
| 2.50% | CBD lost with waxes |

| | | | | |
|---|---|---|---|---|
| 1.50% | CBD lost in desolvation | | | |
| | | 1 | 2.3 | w/v CBD to alkane |

| | |
|---|---|
| 0.10% | w/w Catalyst |
| 1.00% | Seed crystal |

| | | | | |
|---|---|---|---|---|
| | | 1 | 2 | v/w alkane wash to CBD |
| 80.00% | CBD Crystallization yield | | | |
| | | 2 | 1 | v/w water wash to CBD |

Fig. 4

ISOLATION AND CRYSTALLIZATION OF CANNABINOIDS WITHOUT DISTILLATION OR EVAPORATION OF SOLVENTS

CROSS-REFERENCE TO PRIOR APPLICATIONS

The present application is based on and claims the benefit and priority of U.S. Provisional Patent Application Ser. No. 63/186,695 filed on 10 May 2021.

U.S. GOVERNMENT SUPPORT

N/A

BACKGROUND OF THE INVENTION

Area of the Art

The present application is in the art of extracting cannabinoids from cannabis plant material and is more specifically directed to a process that produces crystallized cannabinoids without distillation or solvent evaporation steps.

Description of the Background Art

The cannabis plant (*Cannabis sativa* L.) has a long history of being a plant with important herbal and medical properties. Although the plant fell into disfavor in many Western countries, the medical and recreational properties of cannabis plant material have recently been rediscovered with several countries as well as U.S. States legalizing medical, and in some cases, recreational use of cannabis. Traditionally, cannabis has been ingested either by smoking or by eating foods containing ground cannabis material. Neither of these routes of administration are particularly adapted to controlled medical applications. The traditional smoking-based routes of administration are being supplanted by oral consumption or inhalation (by means of a vaporizer device) of cannabis extract. Currently, extracts (often called cannabis oil) are produced by a variety of related processes. These processes all use a solvent (or solvent mixture) to extract (dissolve) active cannabis constituents from herbal material. In most cases, the solvent is an organic solvent such as a hydrocarbon or alcohol; however, supercritical carbon dioxide is also used. Generally, the solvent dissolves waxes/lipids and pigments from the plant material which waxes/lipids and pigments are not desired in the final extract and must be removed. Then, the original solvent is recovered for reuse and the crude cannabis oil is further fractionated by distillation. These extraction processes are energy and time intensive and are generally more suitable for batch, as opposed to continuous, processing. What is needed is a cannabis extraction process that avoids the bottleneck of distillation and is adapted to a continuous processing of the extract.

SUMMARY OF THE INVENTION

The inventive process extracts cannabis plant material with a solvent matrix consisting of one or more organic solvents and optionally water. The cannabis plant material (usually chopped or reduced to centimeter or millimeter-sized pieces) is agitated in the solvent matrix and then removed by filtration, centrifugation or similar separation techniques. The solvent matrix generally contains organic solvents and water, but if wet plant material is extracted, the water can be omitted from the solvent matrix because the plant material provides water. Following extraction, the plant material is separated from the solvent matrix by centrifugation. The resulting extract is clarified by filtration. This can be achieved by membrane filtration which also removes most of the water and water-soluble impurities. The resulting extract is dewaxed using membrane filtration and/or liquid-liquid extraction. Excess solvent and terpenoids are removed by means of molecular weight cutoff membrane filtration and the resulting cannabinoid solution is decarboxylated catalytically. Finally seed crystals are added and the extracted cannabinoids are crystalized.

DESCRIPTION OF THE FIGURES

FIG. 2 shows an outline of the process illustrating component recovery at each step;

FIG. 3 shows running totals of component recovery; and

FIG. 4 shows a summary of yields and material lost at each step.

DETAILED DESCRIPTION OF THE INVENTION

Figure 1:
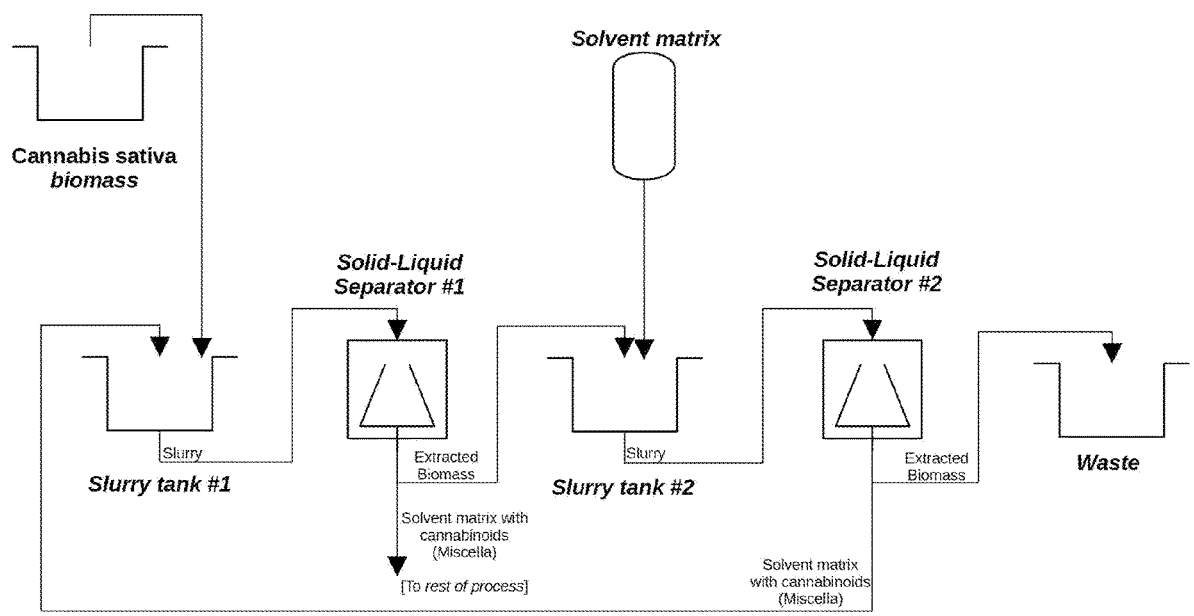
FIG. 1 shows a simplified diagram of a part of the overall process to illustrate organic solvent and/or water use in successive batches.

The following description is provided to enable any person skilled in the art to make and use the invention and sets forth the best modes contemplated by the inventor of carrying out his invention. Various modifications, however, will remain readily apparent to those skilled in the art since the general principles of the present invention have been defined herein specifically to provide a cannabis extraction process that produces a crystalline cannabinoid product that reclaims solvents without using distillation or other evaporation-based techniques.

As shown in FIG. 1 the cannabis plant material is first extracted with a solvent matrix. The solvent matrix generally contains organic solvents and water, but if wet plant material is extracted, the water can be omitted from the solvent matrix because the plant material provides water. Following extraction, the plant material is separated from the solvent matrix by centrifugation. The resulting extract is clarified by filtration. This can be achieved by membrane filtration which also removes most of the water and water-soluble impurities. The resulting extract is dewaxed using membrane filtration and/or liquid-liquid extraction. Excess solvent and terpenoids are removed by using molecular weight cutoff membrane filtration, and the resulting cannabinoid solution is decarboxylated catalytically. Finally seed crystals are added and the extracted cannabinoids are crystalized.

Extraction.

The inventive process starts out with milled or chopped cannabis material. Depending on which cannabinoid or other natural cannabis constituent is of interest any portion of the cannabis plant can be used, but in most cases the preferred starting material is all or some portion of the inflorescence of the "female" (i.e., pistilate) plant is used because the majority of cannabinoids and other biologically active molecules are found in the trichomes of the inflorescence. The plant material is preferably milled or chopped into small (e.g., ranging from a few square millimeters to a few square centimeters) pieces. It will be understood that the optimum particle size is influenced by the structure of the extraction device. If the extraction device is a flow through arrangement, pieces of the plant material that are too small can clog the device thereby slowing or stopping flow. Excessively large pieces may not favor complete extraction so that a longer extraction period with a different optimum water to solvent ratio as well as different solvent(s) may be required. If the extraction is accomplished by immersion with agitation particle size will impact removal of the extract from the biomass. In many traditional extraction schemes the cannabis is extracted with pure or nearly pure organic solvents. In the current process the cannabis mixture is preferably extracted in a slurry by a solvent matrix—a mixture (an emulsion assuming that the solvent is not miscible with water) of a solvent and water—the currently preferred solvent is a mixture of organic solvent(s) and water although water-free solvent(s) can be used. It should be kept in mind that the pH of the final extraction fluid is important because alkaline water may preferentially pick up more biopolymers and other undesired compounds. Moreover, care must be taken to not make the water so alkaline that it converts the cannabinoids to salts in which case the cannabinoids will dissolve into the water phase rather than the organic solvent phase as is desired. As mentioned below, fresh, undried plant material can be used in which case not as much water would be added to the solvent because the fresh, hydrated plant material would absorb less water from the solvent matrix. Adding some type of salt to the water may improve later separation of water from the organic solvent. An advantage of adding water to the extraction liquid is the ability to wet and mix a much larger volume of cannabis biomass without having to increase the volume of organic solvent. Generally, water is added to the solvent at a ratio of between 1:5 and 5:1 parts water per parts solvent. The ratio is adjusted depending on whether the cannabis material is wet or dry and on the cannabinoid content of the cannabis. The appropriate organic solvents are liquid alkanes such as pentane, hexane and heptane although other hydrophobic hydrocarbons are suitable. The hydrophobic active *Cannabis* constituents will dissolve into the organic solvent while more hydrophilic components (many of them undesirable impurities) will dissolve into the aqueous phase. The extraction preferably takes place at room temperature although the extraction temperature can be raised or lowered to control the rate of extraction of various components.

The use of a hydrophobic extraction solvent also means that the process can be applied to "raw" (i.e., undried) biomass. It is possible to harvest the growing cannabis plants, ideally remove the main stalk (i.e., "buck" the plant) and remove as many fan leaves (which contain only low concentrations of cannabinoids) and secondary stems as possible. Alternatively, the entire plant can be processed. The resulting material is shredded or chopped into approximately 2 cm pieces and then soaked and agitated in the solvent mixture. The larger the plant pieces, the longer the extraction takes.

Separation-Clarification.

After extraction is complete, the biomass slurry is pumped through a separation system to separate the liquid extract from the biomass. The two most common methodologies for separation are screw-type presses and decanter centrifuges. However, both of these tend to leave the biomass too wet while screw presses may actually squeeze out undesirable compounds into the extract. These shortcomings can be overcome with the use of a horizontal peeler type centrifuge. In a preferred embodiment an initial slurry is made using solvents that have already done a single extraction; this is pumped through a horizontal peeler centrifuge, and the liquid micellar fraction is sent for further processing. The extracted solid fraction may optionally be washed using fresh solvent and/or water, for example, by spraying on a conveyor, or in a second agitation/extraction tank, and the wash fluid processed in the same manner as the initial extract. (See discussion of FIG. 1, below.) The resulting extract is then clarified using a filtration system to remove small insoluble particles. This can be achieved with membrane filters—for example tangential flow filtration which can also remove essentially all the water (and water-dissolved impurities) from the extraction fluid. This separation can also be performed with disc centrifuges, tubular centrifuges, depth filtration or other mechanical means.

Dewaxing.

Besides the desired cannabinoids, the organic solvent also extracts waxes, other lipids and other hydrophobic compounds that are not desired in the product. In traditional extractions these components are frequently removed by "winterizing" which is a process in which the extract is refrigerated to a very low temperature so that waxes and lipids come out of solution (i.e., precipitate) and can be removed by filtration. The instant process uses membrane filters (depending on the exact process parameters membranes with a molecular weight cutoff of 500-6,000 Da may be used) to remove the waxes/lipids either at room temperature or with slight chilling to about 5° C. The waxes/lipids can also be removed by means of a liquid-liquid extraction from the extraction solvent to one that has a high affinity for cannabinoids and a low affinity for fats and waxes. Methanol is generally the ideal solvent for this process.

Solvent/Terpenoid Removal.

At this point one has clarified organic solvent in which cannabinoids and other hydrophobic cannabis components (such as terpenoids) are dissolved. In traditional extractions short path distillation is used to remove the organic solvent and terpenoids. The solvent and terpenoids are separated by distillation and the solvents recycled. The terpenoids can be used in some cannabis end products or discarded. In the current process membrane filtration is used for desolvation to separate the solvent and terpenoids from the dissolved cannabinoids. Generally, the idea is to select a membrane with a molecular weight cutoff (MWCO) that allows smaller molecules such as solvents to pass while retaining the cannabinoids. The generally useful range is a cutoff between about 25 Da and 1000 Da although most process steps use MCWO between about 250 and 600 Da. Unfortunately, the MCWO specifications from one manufacturer or one style of membrane do not exactly translate to another membrane style or membranes from a different manufacturer. In terms of membrane types, spiral wound membranes are generally closer to optimal than others for the instant process, but hollow fiber, tubular, capillary, or ceramics can be successfully used. In the inventive process solvent-terpenoid separation may occur in two stages. In the first bulk removal stage, solvent and terpenoids are removed from the extract. The recovered solvent and terpenoids are sent to secondary recovery, where most of the solvent is removed from the fluid, leaving approximately a solution that is about 1:1 solvent to terpenoids. This solution can then be evaporated in the traditional manner (distillation, rotary evaporation, etc.) to recover the solvent or the terpenoids, or both, if desired. However, the initial solvent/terpenoid removal may occur before rather than after the Dewaxing step depending on exact process set up parameters employed. If methanol is used with liquid-liquid extraction for the dewaxing step (see above), it is also possible to add water to the cannabinoid-methanol solution (about five to seven volumes water per one volume of methanol-cannabinoid solution) and perform a liquid-liquid extraction against a liquid alkane with the cannabinoids transferring to the alkane.

Decarboxylation.

The cannabis plant synthesizes a cannabinoid as the corresponding carboxylic acid. Thus cannabidiol (CBD) is synthesized as cannabidiol acid (CBDA). Generally, the acid forms of cannabinoids are not physiologically active so they must be decarboxylated. The acid cannabinoids spontaneously decarboxylate at elevated temperatures (at temperatures above about 100° C.) so that distillation steps usually result in decarboxylation. In the current process an insoluble catalyst is added to achieve decarboxylation without having or distill the product or heat it above about 60° C. Magnesium oxide is the currently preferred catalyst although other basic metal oxides, alkoxides or salts can be used. Magnesium oxide is insoluble in organic solvents and can be removed by filtration, centrifugation or by altering the pH of the solution to render the catalyst fully water soluble. Currently, the decarboxylated solution is washed with water (to remove any water-soluble impurities) or centrifuged to remove the catalyst. Washing with a brine solution (as opposed to pure water) may cause some improvement. If the methanol dewaxing method (explained above) is used, this aqueous washing step occurs prior to the methanol dewaxing.

Crystallization.

At this point in the extraction scheme decarboxylated cannabinoids relatively free of impurities exist in a solvent solution. While it is possible to further purify the cannabinoids by means of distillation, the preferred process avoids distillation by crystallizing the cannabinoids. The solution containing the cannabinoids is refrigerated to between about −5° C. and 5° C. A quantity (currently it is believed that seed crystals weighing about 1% to 5% of the cannabinoid content of the cannabis material) of seed crystals is added (often as a slurry in organic solvent) and the temperature is further lowered to between about −15° C. and −35° C., and the mixture stirred until crystallization is complete. These temperatures are ideal for a pentane-based solvent system. If a heptane- or hexane-based solvent is used, the ideal temperatures are somewhat higher with the finishing temperature being about 0° C. to 10° C. The crystallized cannabinoid is removed by filtration, and the crystals are washed with cold organic solvent (too cold to dissolve an appreciable quantity of cannabinoid) and then optionally, cold water. Solvent is recovered for reuse by membrane filtration as in the Solvent Removal step (above). In the situation where the extract contains a significant quantity of more than one cannabinoid, seed crystals of the other cannabinoid(s) can be used to harvest those cannabinoids. Finally, residual organic solvent is reclaimed by membrane filtration. It will be appreciated that the precise size and quantity of seed crystals depends on the desired end product. The seed crystals are ideally added when the crystallization solution is between one and three degrees below the temperature where the solution has first reached the solubility limit, and the crystallization solution is within the metastable zone. It may be beneficial to apply thermal cycling within the metastable zone, thereby forcing Ostwald ripening to enhance the finished product's purity and crystal structure. Depending on the desired finished product, a multi-stage crystallization process can be effective. Usually performed as one fast crystallization to get the bulk of the product out, then a second (or more) crystallization to enhance crystal structure and product purity.

FIG. 1 shows a simplified diagram of a part of the extraction process to illustrate solvent recovery with multiple successive batches. In the drawing each batch of cannabis biomass is extracted twice to enhance recovery of cannabinoids. Fresh biomass is added to Slurry tank #1 and extracted with solvent matrix recovered from the previous batch of cannabis biomass by Solid-Liquid Separator #2. After appropriate incubation with the solvent matrix, the resulting mixture is pumped into Solid-Liquid Separator #1. The solvent matrix along with dissolved cannabinoids is sent on to the remaining processing steps. The wet biomass is placed in Slurry tank #2 and fresh Solvent matrix is added. After appropriate incubation, the slurry is pumped into Solid-Liquid Separator #2. The reclaimed solvent matrix is pumped back to Slurry tank #1 to extract a fresh batch of biomass, and the extracted biomass is sent to waste. It will be understood that second extraction can be skipped in which case the extracted biomass from Solid-Liquid Separator #1 is sent directly to waste.

FIG. 2 shows an outline of the entire inventive process being used to recover CBD crystals from a high CBD cannabis strain. Amounts of various ingredients and their recovery is shown. FIG. 2 start with 200 kg of milled cannabis which contains 12 kg of CBD by analysis. The extraction fluid contains 680 L of alkane solvent (heptane) and 1000 L of water. After extraction and separation 175 kg of cannabis biomass is recovered. The waste contains about 12 L of heptane and 50 L of water. Based on the CBD content of the separated extractant about 0.32 kg of CBD are lost along with the 12 L of heptane. The Clarifying filtration recovers about 9 kg of additional biomass which holds about 6 L of heptane which contains a further 0.2 kg of CBD. The filtration process also removed about 950 L of water so that the solution being dewaxed is largely devoid of water. In the Dewaxing step about 0.4 kg CBD is dissolved in/bound to the removed waxes and lipids and is lost.

The Solvent Removal (Desolvation) process recovers about 548 L of heptane which contain around 0.2 kg of CBD. Following the catalytic decarboxylation step 34.3 L of water are used to remove the catalyst. Optionally, brine rather than pure water can be used in this washing step. The seed crystals (0.61 kg) are added in a 0.4 L alkane slurry, and the crystallization proceeds as described above. The crystals are recovered by filtration and washed with 24 L of cold water and 8 L of cold alkane. About 42 L of heptane (which represents the diluted mother liquor—original clarified and dewaxed extract) are recovered and contain about 3 kg of uncrystallized CBD while about 12 kg of CBD crystals are recovered. Considering that 0.61 kg of seed crystals were added, 12 kg of the original 16 kg of CBD are recovered for a yield of about 80%. FIG. 3 shows running totals of the various components present in each step while FIG. 4 shows a summary of yield and material lost during the process as well as ratios of solvent to biomass or CBD at various stages.

The following claims are thus to be understood to include what is specifically illustrated and described above, what is conceptually equivalent, and what can be obviously substituted. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A process for producing crystallized cannabinoids without solvent evaporation steps comprising the steps of:

providing cannabis material;

immersing the cannabis material in a solvent matrix to produce a first extract;

separating the cannabis material from the first extract;

clarifying the first extract to remove insoluble material and water to produce a clarified extract;

dewaxing the clarified extract using membrane filtration;

removing using membrane filtration to remove solvent;

using a catalytic decarboxylating agent to produce a decarboxylated extract;

crystallizing cannabinoids from the decarboxylated extract; and harvesting crystallized cannabinoid.

2. The process of claim 1, wherein the solvent matrix is a mixture of one or more organic solvents and water.

3. The process of claim 1, wherein the solvent matrix is a mixture of one or more organic solvents.

4. The process of claim 1, wherein the step of removing precedes the step of dewaxing.

5. The process of claim 1, wherein the step of dewaxing also includes liquid-liquid extraction with methanol.

6. The process of claim 1, wherein the step of crystallizing cannabinoids includes adding seed crystals.

* * * * *